(12) United States Patent
Williams, II et al.

(10) Patent No.: US 6,791,088 B1
(45) Date of Patent: Sep. 14, 2004

(54) INFRARED LEAK DETECTOR

(75) Inventors: William J. Williams, II, Melbourne, FL (US); Glenn A. Dejong, Merritt Island, FL (US)

(73) Assignee: Twin Rivers Engineering, Inc., Melbourne, FL (US)

( * ) Notice: Subject to any disclaimer, the term of this patent is extended or adjusted under 35 U.S.C. 154(b) by 105 days.

(21) Appl. No.: 10/138,399

(22) Filed: May 3, 2002

Related U.S. Application Data

(60) Provisional application No. 60/288,857, filed on May 4, 2001.

(51) Int. Cl.[7] .............................. G01J 5/02; G01M 3/04
(52) U.S. Cl. ....................................... 250/343; 250/345
(58) Field of Search ................................ 250/343, 345, 250/338.5; 73/40, 40.7, 49.1, 49.2; 340/605, 539, 632, 491.6, 693.5, 635, 363, 464, 455; 356/437, 414

(56) References Cited

U.S. PATENT DOCUMENTS

| | | | | |
|---|---|---|---|---|
| 4,489,239 A | * | 12/1984 | Grant et al. | 250/339.03 |
| 4,825,079 A | * | 4/1989 | Takamatsu et al. | 250/338.3 |
| 4,958,076 A | * | 9/1990 | Bonne et al. | 250/343 |
| 5,156,042 A | * | 10/1992 | Carlin et al. | 73/49.2 |
| 5,228,329 A | * | 7/1993 | Dennison | 73/49.1 |
| 5,264,833 A | * | 11/1993 | Jeffers et al. | 340/632 |
| 5,497,003 A | * | 3/1996 | Baliga et al. | 250/338.3 |
| 5,889,199 A | * | 3/1999 | Wong et al. | 73/40 |
| 6,362,741 B1 | * | 3/2002 | Hickox et al. | 340/605 |
| 6,509,567 B2 | * | 1/2003 | Boudet et al. | 250/345 |
| 2002/0007663 A1 | * | 1/2002 | Scaringe et al. | 73/40.7 |
| 2002/0033759 A1 | * | 3/2002 | Morello | 340/605 |
| 2003/0086091 A1 | * | 5/2003 | Hinnrichs et al. | 356/436 |

* cited by examiner

*Primary Examiner*—Constantine Hannaher
*Assistant Examiner*—Otilia Gabor
(74) *Attorney, Agent, or Firm*—Brian S. Steinberger; Law Offices of Brian S. Steinberger

(57) ABSTRACT

A leak detector using an infrared emitter and pyroelectric sensor to form an instrument for identifying the presence and concentration of a selected material type gas compound, such as a refrigerant gas compound within a given sample, such as a sample of ambient air. For the detection, a radiation flux coming from an infrared emitter penetrates the sample, which is analyzed spectrally, and results in a wave length-specific signal being generated at the output of the detector. By controlling the type of optical filter, the radiation energy is controlled at a selected wavelength, to ensure coverage of all selected compounds. For refrigerants, the selected wavelength can be between approximately 8 to approximately 10 microns in the wavelength range. This selected wavelength obscures other signals, thus minimizing false alarms. By not chopping or pulsing the emitter, the leak detector has a faster response time with no adverse impacts on the accuracy of the compound material being detected. To further minimize false alarms and to ensure that the emitter does not come in contact with the sample gas, an additional filter can be positioned in the optical path. For refrigerant compounds, the filter can block out signals below approximately 6 microns. For detecting refrigerants, two filters can be used: 1) a broadband filter to allow detection of all refrigerants currently on the market, and 2) a narrowband filter to limit detection only to $R134_a$ which possesses a narrow wavelength, so that detection of other compounds (or contaminants) can be minimized.

14 Claims, 12 Drawing Sheets

Hand-Held Leak-Detector Block Diagram

INFRARED LEAK DETECTOR

This invention relates to gas leak detection, and in particular to methods and devices using infrared optical chambers with circuits in a portable gas leak detector, and this invention claims the benefit of priority to U.S. Provisional Application 60/288,857 filed May 4, 2001.

BACKGROUND AND PRIOR ART

Leak detectors have been used for many applications which include detecting the concentration of specific types of gases. However, using the detector to analyze certain types of gases such as refrigerants, and the like, raises safety and environmental concerns. For example, a leak detector can be designed to detect the concentration of refrigerant gas in surrounding ambient air. This application is important, as leaking refrigerant gas can pose a threat to both health and the environment. As used herein, the term gas refers to any gaseous matter and may refer to, e.g., a combination of elemental gasses, and e.g., (ambient atmospheric gas "air").

Previous portable leak detection equipment use Heated Diodes, Negative Corona Discharge, and other techniques. However, problems existed with these technologies. For example, short sensor life and false alarms have been usual problematic results.

Although infrared technology has existed for many years, infrared technology has not been previously used for leak detection applications for many reasons. For example, manufacturing costs would have made the use of infrared technology too expensive to be used as a leak detector.

A "closed path" type refrigerant monitor has been previously proposed for passing a modulated light beam through a gas to be analyzed and then to an optical detector, all within a closed optical chamber. The detected light is analyzed to provide information about the gas (for example, concentration). The detected light energy may be bandwidth limited such that a specific range of wavelengths is detected to facilitate analysis of particular gasses. However, there are known problems with the "closed path" monitors. For example, analysis is complicated by very little light energy being absorbed by low gas concentrations, substantial low frequency noise present in the analysis system and optical losses associated with typical optical pathways.

As one solution, modulation of the light beam has been performed at relatively high frequencies such that a reasonably large signal-to-noise ratio is maintained in the detected signal. However, there are problems with these solutions. Broadband light sources use a filament to produce spectral emission and accordingly, electronic modulation thereof at high frequencies is impractical. The filaments require too much time to heat up and cool down for high-frequency modulation. Therefore, mechanical choppers have been used to provide high-frequency modulation of the optical source. Unfortunately, mechanical choppers consume significant energy, decrease instrument reliability and increase the complexity, size and weight of instruments that they are incorporated within.

Other closed path instruments have operated without a mechanical chopper by using more powerful sources, more sensitive detectors and/or long optical paths (to facilitate increased spectral absorption by the gas analyzed) so that a somewhat lower infrared modulation frequency operation may then become possible. However, these solutions increase the size, cost and/or weight of the instruments to which they are applied.

To date there is no known type of leak detector that operates within a one second or less response time, is portable and battery powered and eliminates the problems described above with the prior art.

SUMMARY OF THE INVENTION

A primary objective of the invention is to provide an infrared leak detector that can be both portable and battery powered.

A secondary objective of the invention is to provide an infrared leak detector that can both portable and electrical cord powered.

A third objective of the invention is to provide an infrared leak detector that can operate within a one second or less response time.

A fourth objective of the invention is to provide an infrared leak detector having a long sensor life that does not become easily degraded by exposure to large leaks or other reactive gases.

A fifth objective of the invention is to provide an infrared leak detector having accurate sensitivity and accurate selectivity with substantially no false readings.

A preferred embodiment of the hand-held (portable) leak-detector uses Infrared technology to sense when the probe passes a leak. The detector can include an infrared (IR) chamber, an air pump to draw an air type sample such as refrigerant gas into the chamber, a pyroelectric sensor for detecting a selected compound from the sample in the chamber wherein all the components are supported within a portable housing that can be supported in a single hand of a user. The air pump can have a flow rate of approximately 500 cc/min to allow for sampling and finding a small leak without needing for the device to be within approximately 0.635 centimeters (approximately ¼ inch) of the leak source.

The IR chamber can include an IR emitter for emitting an IR beam, an IR filter in the path of the beam, an IR (pyroelectric) detector such as back to back piezo capacitors, Lithium Tanalate, and the like for receiving the emitted beam and a reaction tube where the air sample interacts with the IR beam.

The IR-based leak-detection does not attempt to generate or process a signal proportional to the actual level or concentration of Refrigerant in the probe air stream, but instead maintains a zero signal for any constant level of Refrigerant in the air, i.e., that is not frustrated by background levels of Refrigerant that may have built up, which thus allows more sensitivity to a small leak. The IR beam used in the detector is NOT chopped or pulsed to generate a continuous signal at the detector.

The lack of IR pulsing results in a lack of signal when the air sample is clean (i.e., no gas of interest to detect. On the other hand, the detector and electronics is designed to settle to a d/c equilibrium voltage (which is the same as the zero level set by the user), whenever there is any constant level of Refrigerant. In other words, the instrument is designed to NOT detect a constant level of Refrigerant. Therefore a signal is generated only when there is an increase in the Refrigerant concentration that changes (rapidly) within the time frame the instrument is designed to detect. The time frame for detecting change is in the order of one second for typical leak detectors, which is a typical time that the sampling probe is moved across a few inches of piping and fittings. This time frame also correlates with a significant amount of air from the leak source entering the chamber, at the approximate 500 cc/min flow rate. The instrument detects the increase in concentration associated with approaching a leak, but ignores the background concentration of Refrigerant that may have built up in a room over longer periods of time (minutes and hours). Additional favorable byproducts of this non-pulsed approach is (1) the elimination of mechanical and or electrical devices to perform the chopping, (2) the battery consumption and (3) the cost of these devices, and (4) elimination of the noise associated with and generated by chopping or pulsing the emitter IR beam, including noise from the imperfections or variations in the chopping, and the noise associated with a significant non-zero signal level.

The device eliminates the extra signal processing required to determine a leak condition by comparing many actual measured levels of concentration. The invention produces a signal only and directly from the sudden rise in concentration at a leak, and avoids processing a continuous measurement signal.

The accumulator within the detector is used as a type of peak-detector and can include a resistor R26 that pulls the op-amp's inverting input low, from a nearly constant current sinked to Vee that must be supplied from the amplifier. This therefore keeps the amplifier and diode in an active positive (forward) mode. There are several non-obvious, but important benefits to this accumulator. First, the amplifier is not allowed to operate near zero, where the output diode could turn off, and allow the amplifier to swing negative, causing instability and noise. This forced active-forward mode allows the leak detector to function without a pulsed emitter, and with great sensitivity. (IR systems with pulsed emitters do not face this instability issue, since there is always a signal being generated from the chopped IR at the detector.) The accumulator's output signal decays at a rate determined by C14 and (mostly) R28. This time constant is designed to provide the user with an attention-getting response from even a very small leak.

Another benefit of the forward-active accumulator is that the zero control always operates slightly positive, for any variations in manufacturing and operation, so it can reference (quiet) ground, rather than (far) between Vee and Vcc. This can allow a more precise and stable zeroing, and provides faster zero setting, due to the relatively low resistance to ground.

The Emitter chamber in the detector can be shaped to maximize direction of the IR down the tube (vs. absorption by the wires, header, etc., while at the same time directing the majority of the radiation, that is not initially aligned with the IR tube, to travel down the tube at large angles, with many bounces off the tube surface, so that the optical length is greatly increased. A longer optical length can increase the probability that the IR radiation will interact with a molecule of the gas being detected. This in turn, can increase the signal strength, and decreases the minimum concentration that can be detected.

The detector sensor can be a pyroelectric device that has, in a preferred implementation, matched back-to-back crystals of, for example, Lithium Tantalite. The output of the 2 crystals can tend to cancel each other when at equilibrium, but produce an electrical voltage when the outer element is heated by exposure to IR radiation.

The output of these 2 parallel detectors can be buffered by a JFET. An IR optical filter is just in front of the IR detector, to allow the detector to only "see" the narrow band wavelengths selected for maximum, unique interaction with the Refrigerant. An optical filter is typically placed in the beam-line before the IR interaction tube, to eliminate both large and small wavelength radiation from entering the gas interaction area. This eliminates the chance for this excess energy, out of the band of interest, to interact with foreign gases (e.g., water vapor, CO2) such that re-emission into the band of interest can create noise and false signals.

The air pumps, an electrically noise component, can be isolated from the rest of the device by an IC voltage regulator with filter capacitors on both sides. The sensitive analog circuitry can be powered by a regulated DC/DC converter, with an additional LC filter at both outputs.

The whole leak detector can be powered for several hours from a rechargeable battery, or can be powered continuously from an AC/DC supply module that plugs into 115 Vac or 230 Vac.

Many other types of gases other than refrigerant gas R134a can be detected with the detector. And an extendable bendable probe extension can be used.

Further objects and advantages of this invention will be apparent from the following detailed description of a presently preferred embodiment which is illustrated schematically in the accompanying drawings.

DESCRIPTION OF THE PREFERRED EMBODIMENTS

Before explaining the disclosed embodiments of the present invention in detail it is to be understood that the invention is not limited in its application to the details of the particular arrangement shown since the invention is capable of other embodiments. Also, the terminology used herein is for the purpose of description and not of limitation.

For the invention, "air" can refer to a gaseous sample that may or may not contain any molecules of interest to the user. "Refrigerant" can refer to molecules of the gas with is of interest to the user, i.e., to be detected, but could in some applications be other refrigerants or other compounds of interest such as Methane, gasoline, and the like.

The novel leak detector can be comprised of an infrared (IR) chamber, an air pump to draw in a sample, and electronics to process the signal. The IR chamber can contain an IR emitter, IR filters, an IR sensor, and a reaction tube where the sample air interacts with the IR beam.

Figure 1:
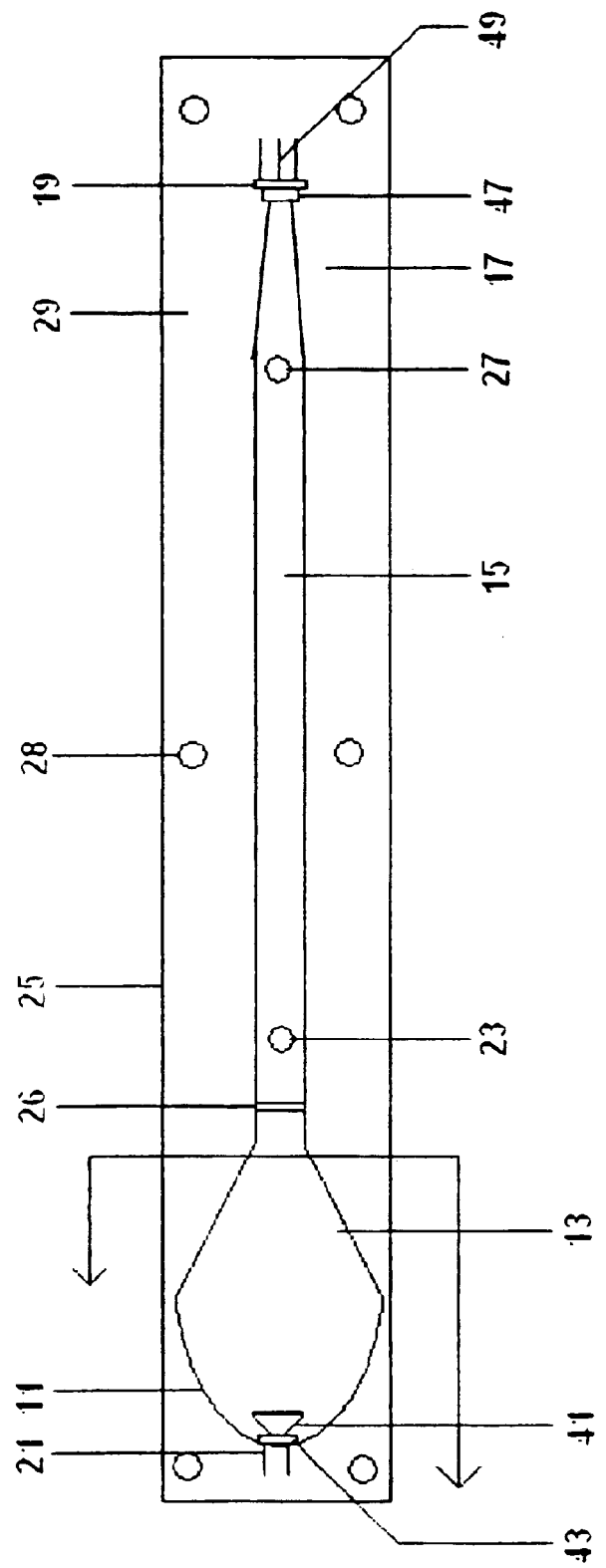
FIG. 1 is a cross-sectional view of an optical chamber with a maize-like folded path that can be used with the subject invention.
Figure 2:
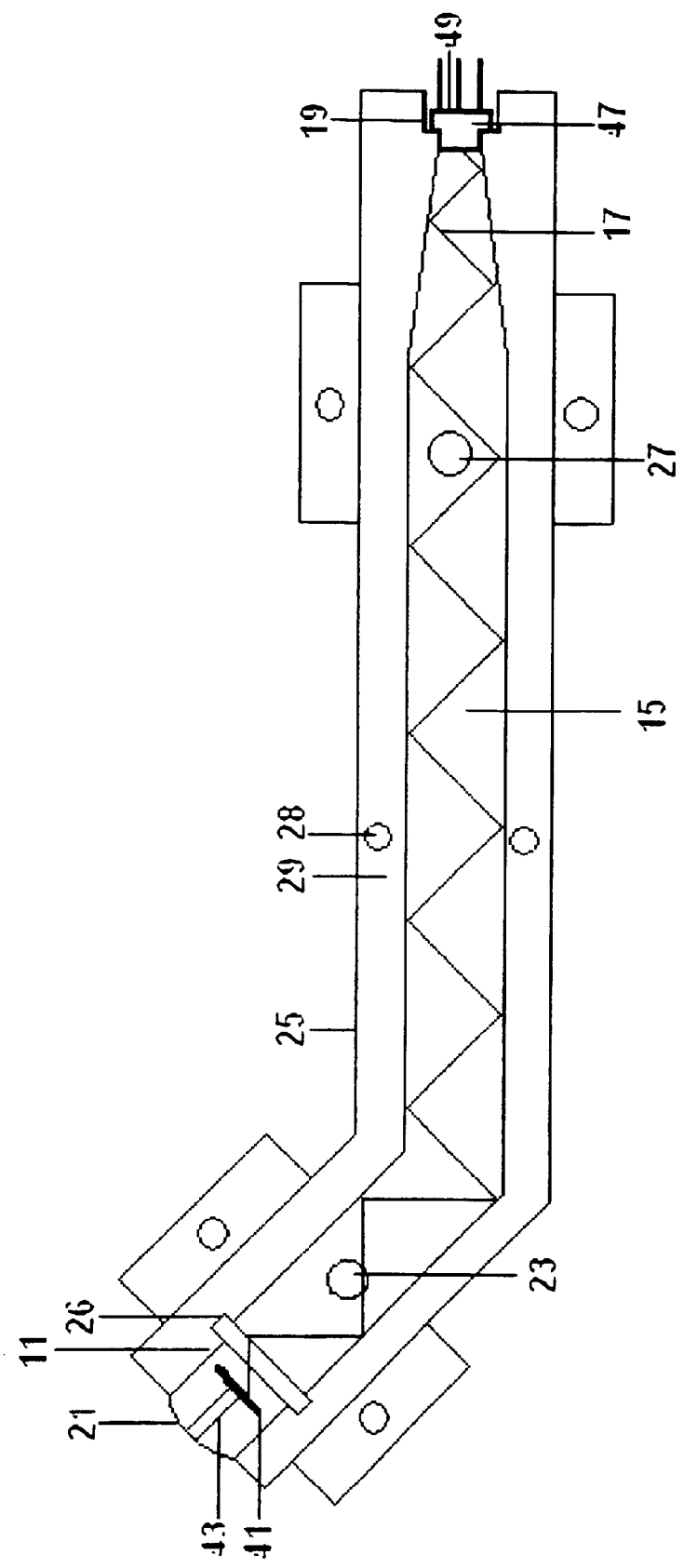
FIG. 2 is a cross-sectional view of another optical chamber that can be used with the subject invention having a bent path.

FIG. 1 is a cross-sectional view of an optical chamber with a maize-like folded path to accomplish long-path behavior in a compact chamber that can be used with the subject invention. FIG. 2 is a cross-sectional view of a bent optical chamber that can be used with the subject invention which can optimize long IR path length behavior by setting an optimum number of reflections by the optimized bend angle. The preferred embodiment of the chamber can be a gold plated chamber. A typical ray trace is shown in FIG. 2.

The portable gas leak detector of the invention can use an optical chamber to efficiently couple infrared(IR) energy from an optical source to an optical sensor, while maximizing IR interaction with the sample material gas. There are several optical chambers that can be used. FIGS. 1–2 are examples of optical chambers that can be used with the novel portable detector of the subject invention. FIG. 2 shows a bent chamber which can optimize long IR path length behavior by setting an optimum number of reflections by the optimized bend angle. FIG. 2 shows an optical chamber which can use a maize-like folded path to accomplish long-path behavior in a compact chamber. Both FIGS. 1 and 2 can allow the volume to be minimized to improve response and recovery times, and retain linear flow of the gas to improve gas clearing time. A description of the components will now be described. Component 11 refers to hemispherical shape, 26 is a first filter, 43 is the infrared(IR) emitter, 23 is the sample air intake port, 25 is the gold plated housing. 28 refers to a fastener such as a screw, and the like. 19 refers to surface for holding the detector in place. 17 refers to the cone shape for directing IR energy. 21 refers to surface for holding the IR emitter. 28 refers to the screw hole for assemblying the housing together. 27 refers to the sample gas outlet to the pump(shown in FIG. 5). 29 refers to plastic housing. 41 refers to IR emitter. 43 refers to seal for emitter. 47 refers to the pyroelectric IR sensor. 49 refers to the seal for the sensor 47.

Referring to FIGS. 1–2, IR energy passes through the hemispherical shape 11 and is directed through thrombone shape into chamber passing through the first filter 26 that blocks energy from approximately 6 microns down. The energy continues through the chamber and is absorbed by sample gas coming from inlet 27 continuing through the chamber through the cone shape directing into the sensor 47. The sensor can be fitted with a bandpath filter having a narrow bandwidth of approximately 8.48 to approximately 9.9 microns that allows energy to pass into the sensor 47 which can pass onto a personal computer for later processing and display, as needed. An airpump(180 shown in FIG. 5) can pull air out of outlet port 27.

The IR emitter can be a resistive metal element that is heated via an electrical current to a temperature where its gray- or black-body radiation is maximized at the band of wavelengths where there is significant and unique interaction with the gas molecules being detected. Although not essential to the operation of IR-based detection, an emitter with a positive temperature coefficient of resistance improves the performance of a battery-powered instrument. With battery voltage typically varying by approximately 20% or more from fully charged to almost discharged, the power consumed, temperature, and emission spectrum for a positive temp-co emitter will vary considerably less than approximately 20%. A thin platinum film on a silicon/silicon oxide, or an alumina surface is an example of a positive tempco resistance, whereas a NiCr resistively heated emitter generally has a small tempco, and so is more suited to an instrument powered from a regulated ac/dc power supply.

The IR can travel down a tube or beam-line where the air sample is drawn in to interact with the IR beam. This tube can be plated with a material that is highly reflective, such as gold and the like, in order to conserve the signal from loss through absorption by the tube walls. The emitter end of the tube can be a chamber shape to insure that most of the emitted IR gets directed down the interaction tube.

One improvement for hand-held leak detectors is to construct the IR chamber such that the emitter end is not aimed down the interaction tube, but instead is aimed at a sharp bend in the chamber that forces most of the IR energy to reflect of the walls of the interaction tube many times before reaching the detector. The zigzag path from the repeated reflections can create a longer IR path length, and increase the probability of absorption by a low concentration of Refrigerant, and thus increase signal strength and sensitivity to smaller concentrations. My method to increase the effective IR path-length can be important to a portable leak-detector, where space is confined.

The IR detector can include an optical filter "window" that is designed to only allow access to IR wavelengths that interact (get absorbed) strongly with the molecule being detected (e.g., Refrigerant). These wavelengths can be called "in-band."

An important feature to the hand-held leak-detector can be a second optical filter. Just prior to the entry point of the air being sampled, the IR beam can pass though an optical filter designed to remove as much "out-of-band" energy as possible, so the remaining IR beam is predominately of wavelengths that interact strongly with the gas of interest. This increases the signal-to-noise ratio of the system, and decreases the likelihood of false readings. Since most of the emitted blackbody radiation energy is typically out-of-band, the filter on the detector element would block it. However this excess energy, if absorbed at the detector filter, causes unwanted heating of the detector, which in itself increases the noise floor of the detector. In addition, some of the out-of-band spectrum can be absorbed with compounds (water-vapor, carbon-dioxide, gasoline vapor, and the like) in the incoming air, and potentially be re-radiated in-band. Any significant variation in these extraneous compounds can cause variations in the energy seen by the detector, and can cause a false response.

The sensor/detector can be a pyroelectric element. A version employed in this leak detector can include a pair of back-to-back piezo capacitor elements. The pair can be configured to cancel any direct temperature effects that they both experience. Only one element can be exposed to the incoming IR energy. If the IR energy changes (decreases due to absorption by Refrigerant molecules), the slight cooling changes the stress in the element, which changes the electrical potential on the element (pair), which in turn gets amplified by the integral JFET amplifier. The output voltage change on the JFET is then processed to interpret the signal.

An air pump can be used to pull the air sample from the probe tip and through the IR chamber. The pump can be supplied from the battery though a voltage regulator and filter, which provides a more steady air flow, and prevents electrical noise from entering the detector electronics.

The signal from the detector JFET can be processed first by an ac-amplifier that is designed to block the dc level of the detector (which can vary widely), and pass only the differential of the detector output voltage, with a time constant tuned to the reaction of the detector, the delta-time of passing a leak, and the time to fill the IR chamber with an incoming air sample (this is a band-pass on the order of one Hz.)

The differential signal can then be amplified and passed to an accumulator, which consists of a small-signal rectifier and integrator with a bleed-back time constant of a few seconds. This can allows a fleeting signal from a very small leak to be held long enough to be processed by subsequent electronics, and then expressed to the user with visual and/or audio alerts long enough to get his/her attention.

The signal from the accumulator goes to another amplifier that provides the user with a zero control to null out any dc drift anywhere in the system, so that the electronics can be tuned to maximum sensitivity. The signal is then passed through a buffer and to a range-control amplifier designed to allow range changes with minimal upset to signal levels. The range control typically provides a 1x, 4x, and 16x increased in output sensitivity (L, M, S range) to the audio/visual electronics. A clamp is provided to prevent large negative voltages from rebound due to very large signals, or due to the operator inadvertently setting the zero control too far the wrong way.

The above analog signal can then be presented to a simple digitizer that turns on LEDs in a bar-graph configuration. A single on-LED(such as a green light) shows the operator that the electronics is correctly zeroed, and ready for use. The larger the leak/signal, more LEDs light up. The digitizer ladder has an exponential response to increase the resolution of more interesting signals, i.e. smaller leaks.

The analog signal can be processed uniquely in several ways at the audio VCO. First, a chirp rate of approximately 1 Hertz occurs when the electronics is correctly zeroed. If the zero is even slightly too high, the chirp rate immediately jumps to approximately 2 Hertz. If the zero control is too low, the chirp is completely suppressed. When a signal (Refrigerant) is detected, the chirp rate increases in proportion to the leak size. If the leak is very large, the chirp turns into a loud steady tone of approximately 3000 Hertz. Even the smallest leak detectable will cause the chirp rate to increase to a minimum of approximately 2 Hertz, which easily catches the attention of the operator. The audio therefore is designed to allow full operation of the leak-detector with the operators eyes fixed on the probe tip, rather than the instruments display.

A low battery warning LED can be provided. Using a precision reference and a voltage divider tailored to the specific type of battery used (e.g., Nickel-Metal-Hydride), the LED is set to go on to warn the operator that approximately 80% of the battery's charge is depleted, so that he/she is more likely to get the unit recharged while convenient, and to avoid deep discharges that can affect the overall life of the NMH battery.

The controls for the device can be a Power-on, audio enable, zero, and range. A charging status LED can be activated when the battery charger supply is plugged into the leak detector. The charging circuit lights this LED brightly when the battery is low, and then dims the LED as the battery nears full charge.

Note that the above description of the electronics details some specific circuit elements used in one preferred embodiment. The invention can be broader than those specifics. For example, as detailed above, the detector output goes to an ac amplifier with a band-pass of approximately 1 Hz. Since no continuous signal is generated, and the IR emitter is not pulsed, the function of this ac amplifier is to produce a signal that represents a change in the dc level from the detector.

Other electronics can do this function as well: taking this differential can be done digitally as well as in analog. For example, another embodiment could be as follows: a minimum amount of analog amplification of the detector, and then an A/D converter, followed by digital processing to determine signal speed and amplitude, and then to generate an output signal that holds and decays at a rate that provides maximum indication to the human user. The functionality could also be done with an analog switched-signal or sampling mode.

Figure 3:
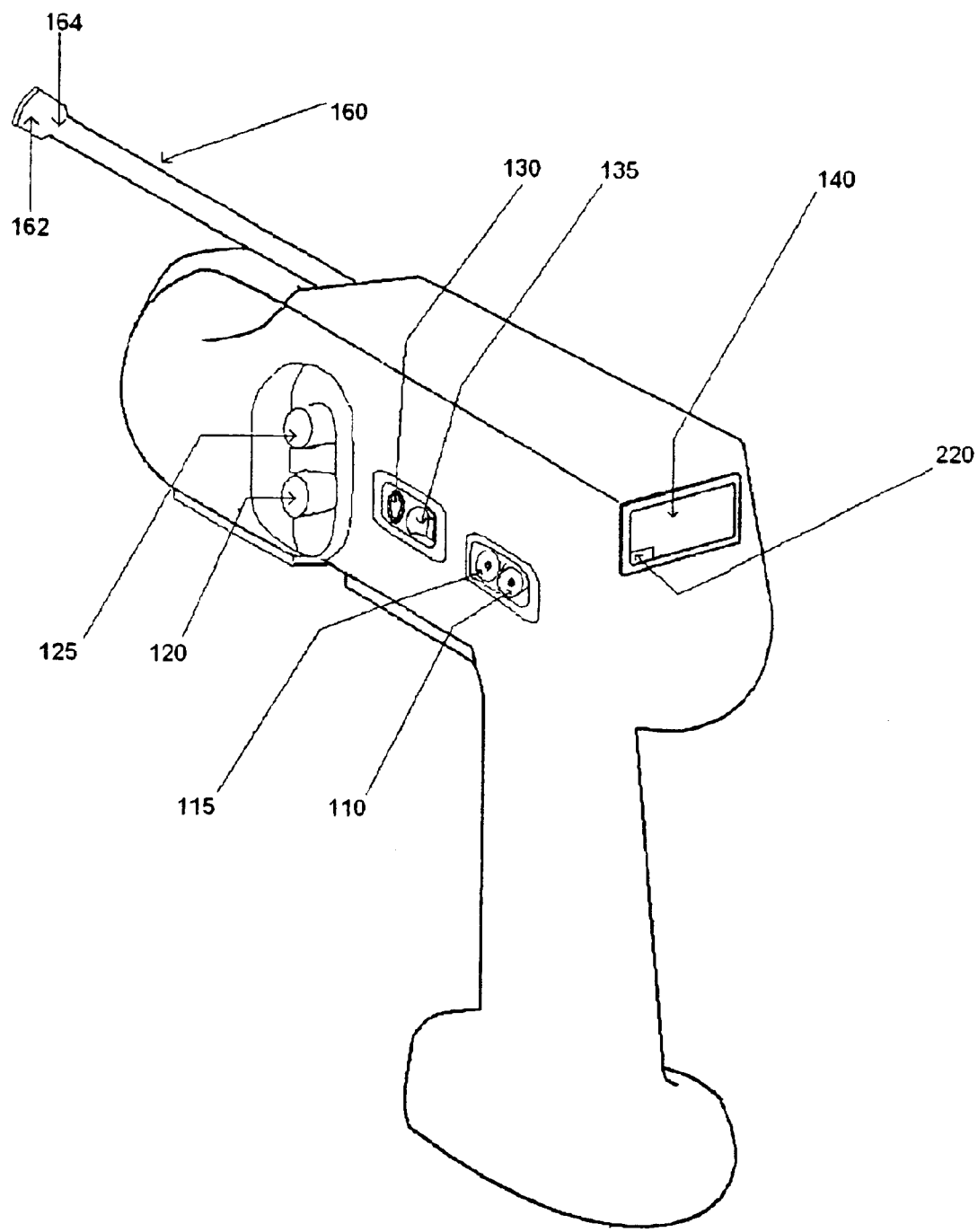
FIG. 3 shows an exterior perspective view of the novel portable detector housing.
Figure 4:
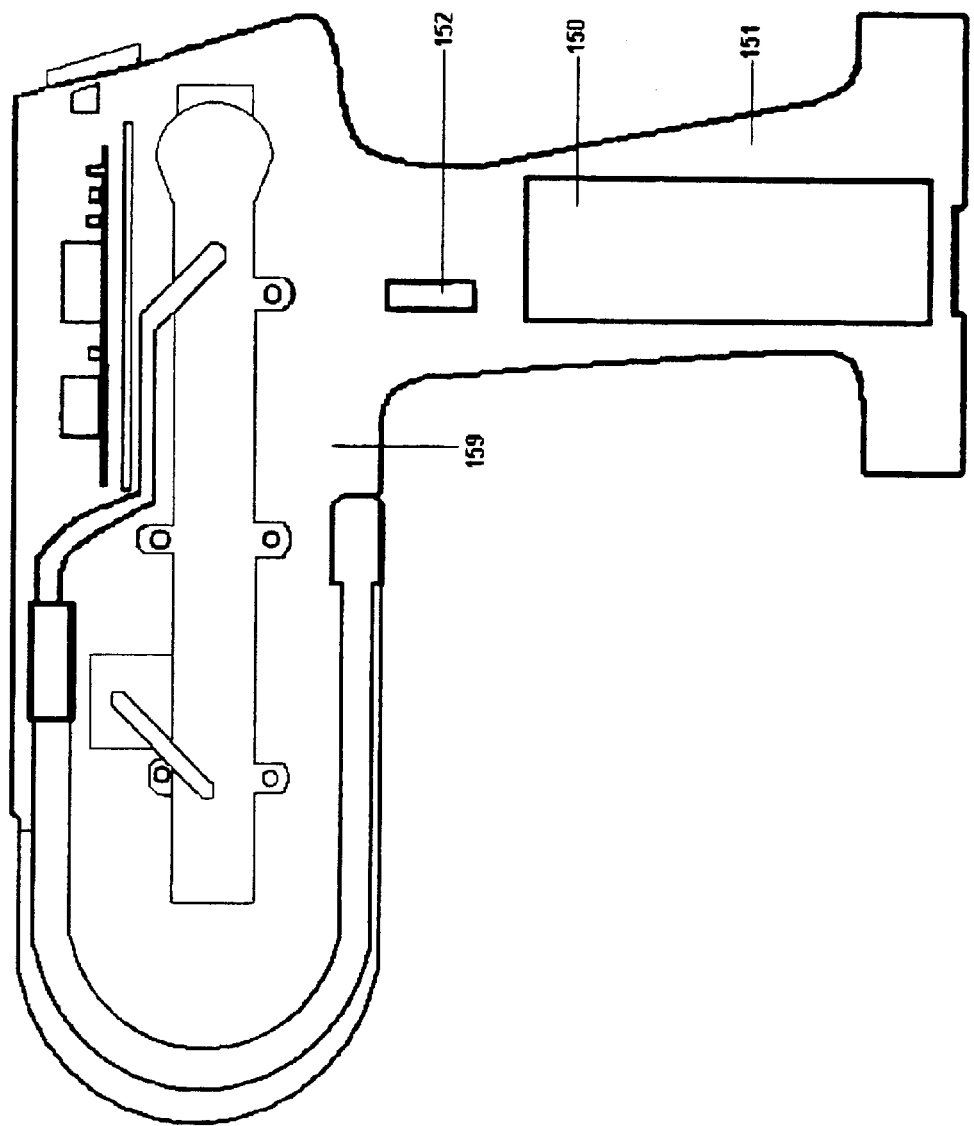
FIG. 4 shows a cross-sectional interior view of the detector housing of FIG. 3.

FIG. 3 shows an exterior perspective view of the novel portable detector housing 1. FIG. 4 shows a cross-sectional interior view of the detector housing 1 of FIG. 3. The housing 1 can be formed from two half shells formed from ABS plastic, and the like, and can be durable and waterproofed in construction.

Referring to FIGS. 3–4, portable detector housing be L-shaped can have a height H of approximately 24.87 centimeters(approximately 9.79 inches) along the hand grip section G to the sensor section S, and a length L, along the sensor section S of approximately 10.322 inches, and can have an overall weight of approximately 31 ounces. A rechargeable battery 150 with battery connector 152 can be located inside the grip section G between a bottom body portion 151 and a top body portion 154. Exterior power cords(not shown) can be attached to an exterior side charger port 130 to charge the battery 150. A charger lamp 135 can light up to varying degrees to indicate when the battery 150 has been sufficiently charged. Facing rearward from the upper sensor section S can be LED display screen 140, with power on/off toggle switch 110 and audio on/off toggle switch 115 on the side of the sensor section S above the grip section G. Rotatable type controls 120, 125(such as but not limited to rheostats, rotating switches and potentiometers, and the like) on the side of sensor section S can be used to respectively adjust sensitivity settings and zero settings of the device 1. On the outside of the device 1 can be an extendable probe 160 which will be explained later in reference to FIG. 9. Other interior components which will be described in more detail later include circuit board 172, board bracket 174 for mounting the circuit board 174, air pump 180, optical bench 185, sample in tube 192, sample out tube 194 and strain relief 195.

Figure 5:
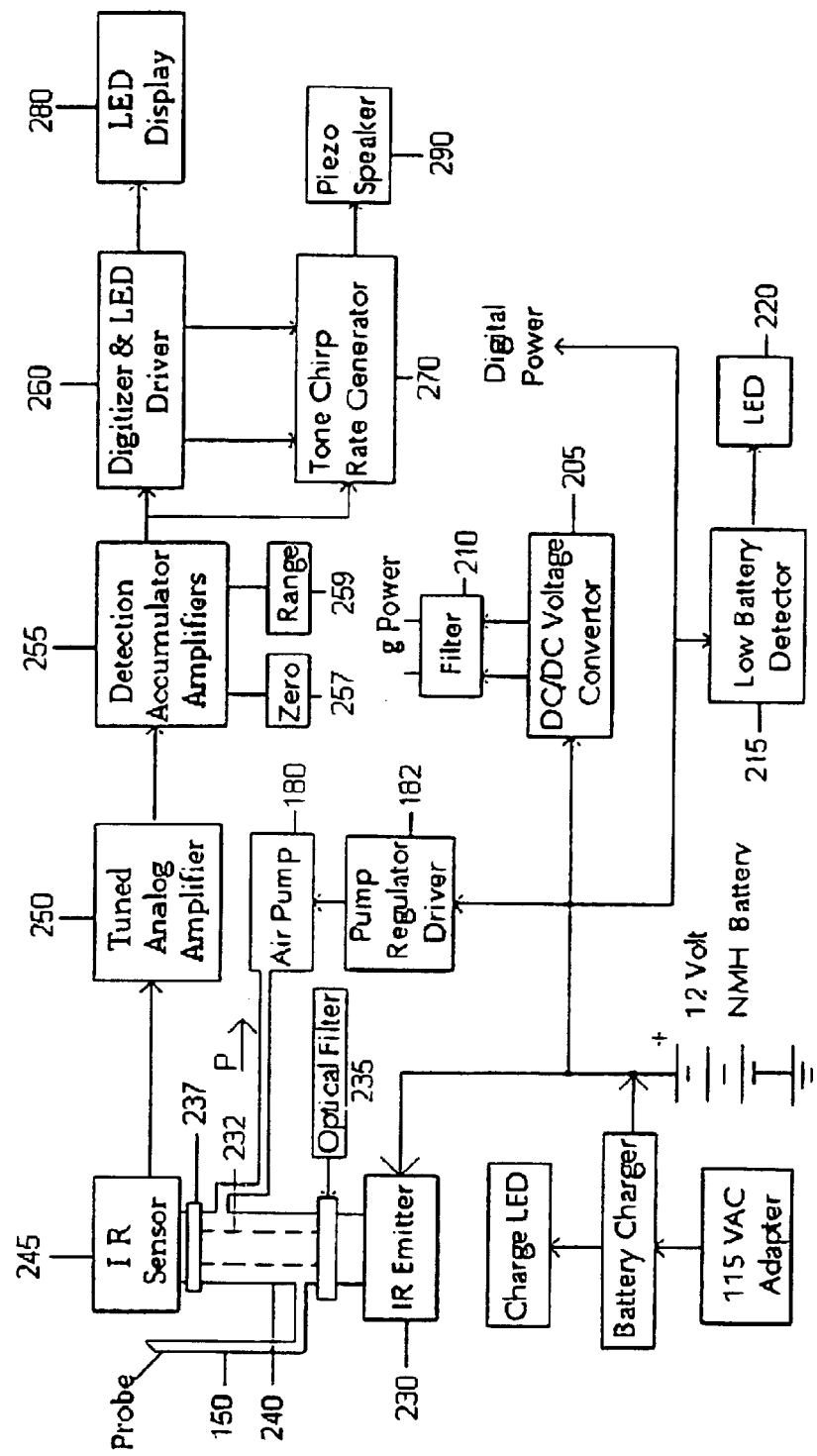
FIG. 5 shows a block diagram of the operational components used in the detector of FIGS. 3–4.

FIG. 5 shows a block diagram of the operational components used in the detector of FIGS. 3–4. FIG. 5 shows a block diagram of a preferred embodiment of the Leak-Detector system. The portable Hand-Held unit is powered by a rechargeable battery 150, such as a Nickel-Metal-Hydride pack that recharges well even if the battery is not fully discharged. The battery 150 can directly power electronics that are not noise sensitive, such as digital, LEDs and the audio. The analog circuitry can be powered via a DC/DC converter 205 and filter(s) 210 to isolate any electrical noise. A low-battery detector 215 can continuously monitors the battery voltage, and warns the user with an LED 220 whose brightness and dimness varies when the battery 150 will soon require a recharge. With the proper selection of battery 150 and Infrared (IR) emitter 230, the emitter 230 can be driven directly from the battery 150. The emitted IR energy 232 must pass through one or more optical filters 235 that select and optimize the IR wavelengths that are most reactive with the species of gas that is being detected. An air pump 180 pulls air in the direction of arrow P continuously from the probe tip 160, and through the IR reaction chamber 240. The pump 180 can be driven by a voltage regulator 182 that keeps the flow-rate independent of battery charge, and also isolates pump electrical noise from the rest of the system.

The probe tip 160 can be a pliable type tip formed from pliable type stainless steel spring material and the like, having a length of between a few centimeters(few inches) and approximately 30.48 centimeters(approximately 12 inches), and can include an enlarged air intake end 162 having a separate filter inside, which can be used to restrict fluids and liquids from entering the probe tip 160.

Just prior to absorption by the IR Sensor 245, the IR beam 232 can pass through another optical filter 237 that is part of the IR sensor assembly. This filter can further improve IR signal to noise ratio and helps isolate the sensor 245 from any thermal changes due to changes in probed air temperature. A third filter 355 or window, shown in the embodiment of FIG. 8, can be attached as a "lid" to the emitter element. This third filter 355 also improves the signal to noise ratio by increasing the in-band energy, and by isolating the chamber 240 from air convection-currents at the emitter, which can create IR "noise" due to handling motion.

Referring to FIG. 5, the IR sensor 245 can include an integral amplifier, such as a JFET follower inside the sensor component. The IR sensor 245 output can be amplified first by a tuned amplifier 250 with a band-pass peak response optimized to approximately 1 to approximately 3 Hertz. Any higher frequencies can be rejected as electrical noise, and slower signals can be rejected as irrelevant environmental changes. The signal next passes through a series of analog amplifiers 255 designed to detect a possibly very small signal (small leak) from the noise of the sensor 245. In addition to greatly increasing the system voltage gain, these amplifiers 255 can favor detection of increases in gas concentration (i.e., dropping IR energy at the sensor 245), accumulate and temporarily hold the signal for the subsequent electronics to process and make alarm (LED display 280(140 FIG. 3) and speaker 290) decisions. A zero control 257(125 FIG. 3) can be provided to set the steady-state "ready" condition. A range switch 259(120 FIG. 2) can allow the user to decrease system gain, and works independently of the zero control, i.e., the range can be switched "on the fly" with no settling time penalty.

Referring again to FIG. 5, the analog output signal can be fed to a simple A/D digitizer 260 and a chirp generator 270. The digitizer 260 is preferably not linear, but is somewhat exponential in response to favor more signal perception resolution with smaller leaks, while avoiding over-running the LED display 280 with moderate-sized leaks. For the LED display 280, Six (6) LEDs, past the green "ready" LED, were found to provide an adequate perception of leak size, in conjunction with the range switch 259. The chirp generator 270 can modulate the tone of the audio (piezo) speaker 290 according to the size of the leak detected. In the steady-state condition (warmed up, but not yet being used) the chirp can be set at approximately 1 beep per second, as an easily recognized condition for the user to know the instrument is properly zeroed and ready to use. (The IR emitter and IR sensor take about one or two minutes to "warm up".) If the zero 257 is set too low, the detector 100 will be less sensitive to leaks, and so the green LED will be off, and the speaker 290 will be silent. When the instrument is ready, the digitizer 260 enables(264) the 1 Hz chirp rate. Upon detection of a small leak, the digitizer 260 can immediately shift(264) the chirp generator 270 to a readily-noticed 2 Hz chirp rate. If the leak is larger, the chirp rate can be increased in proportion to the size of the leak detected.

Figure 6A:
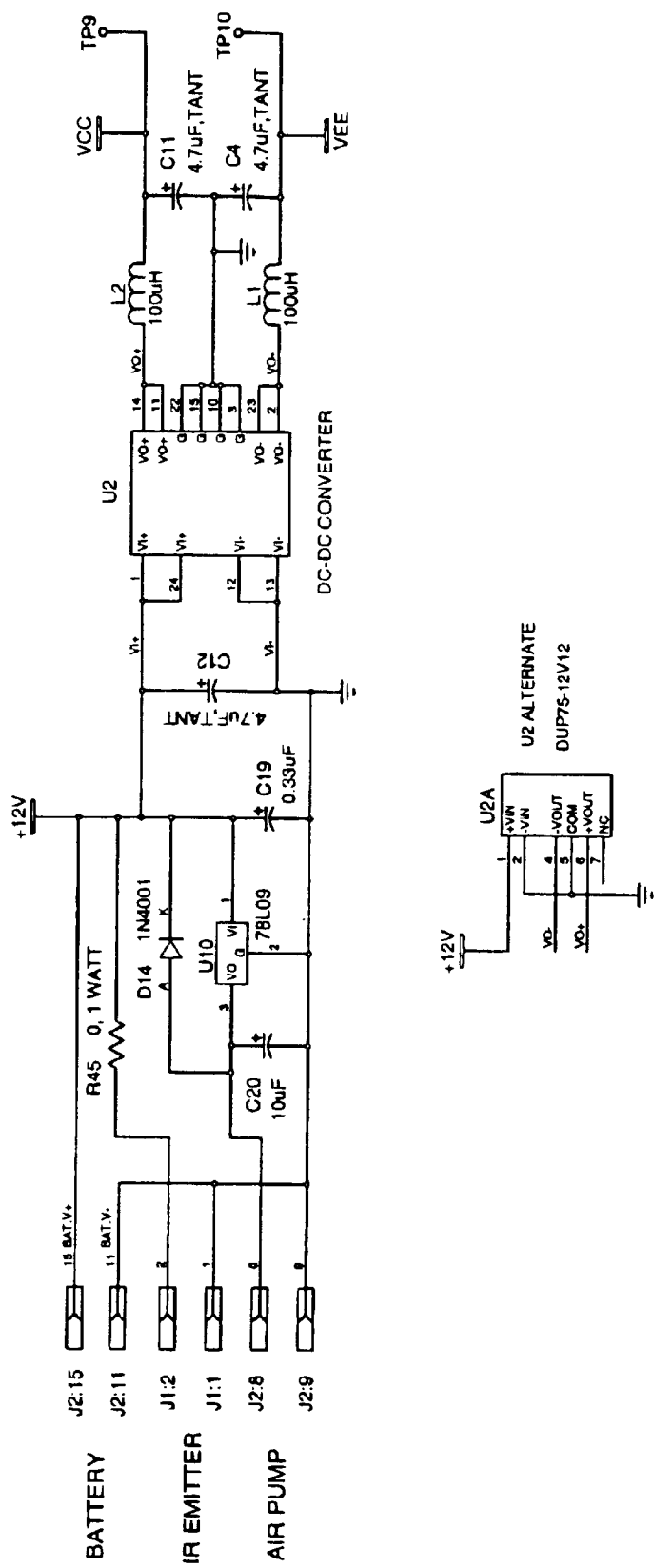
FIGS. 6a, 6b, 6c and 7a and 7b are schematics of the electronic circuitry within the novel detector.
Figure 6B:
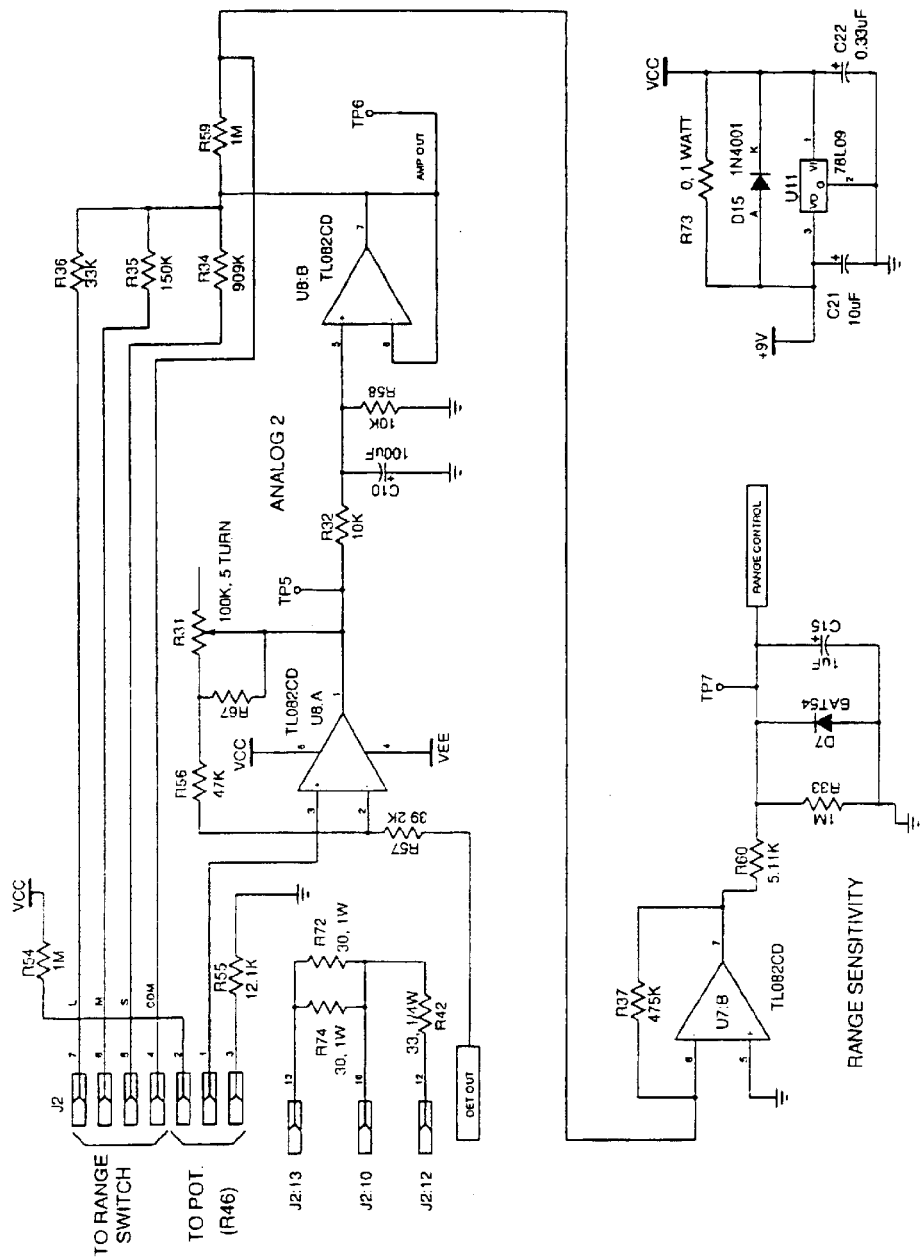
Figure 6C:
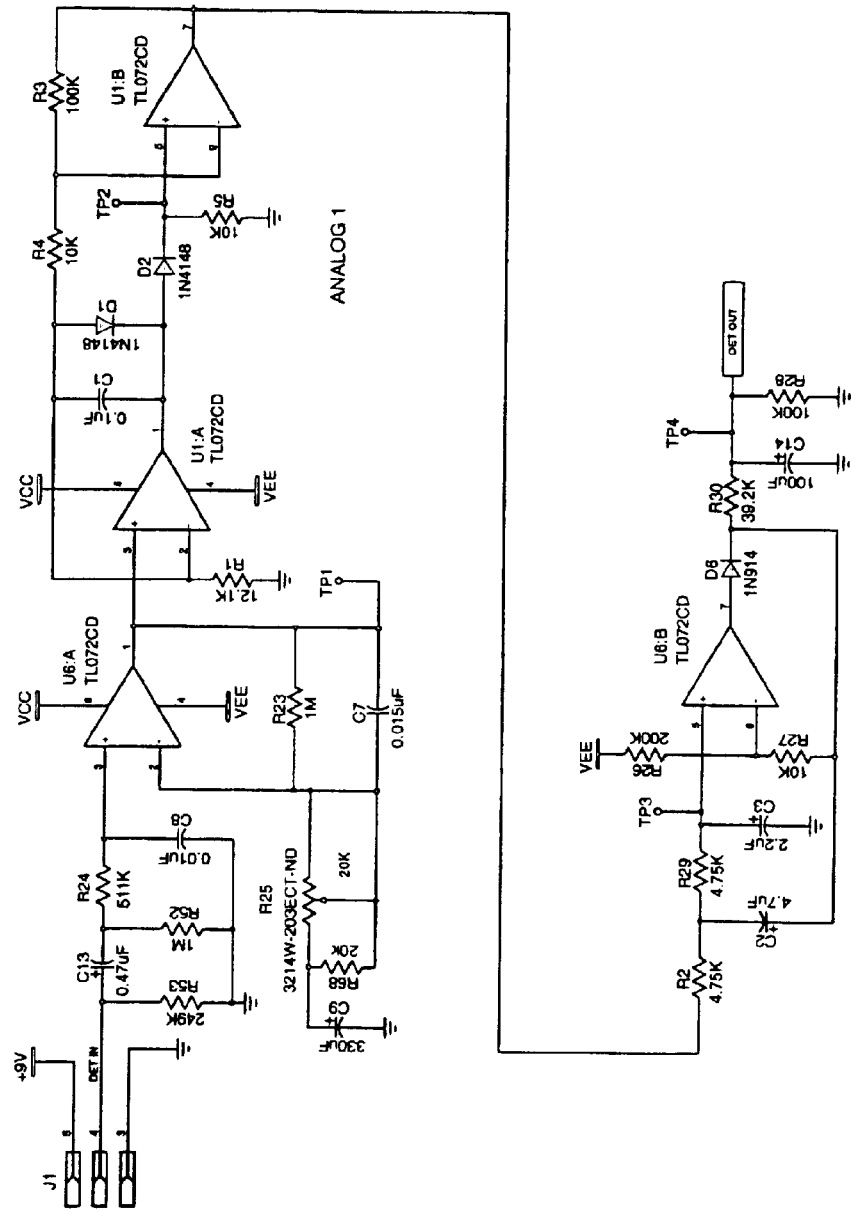
Figure 7A:
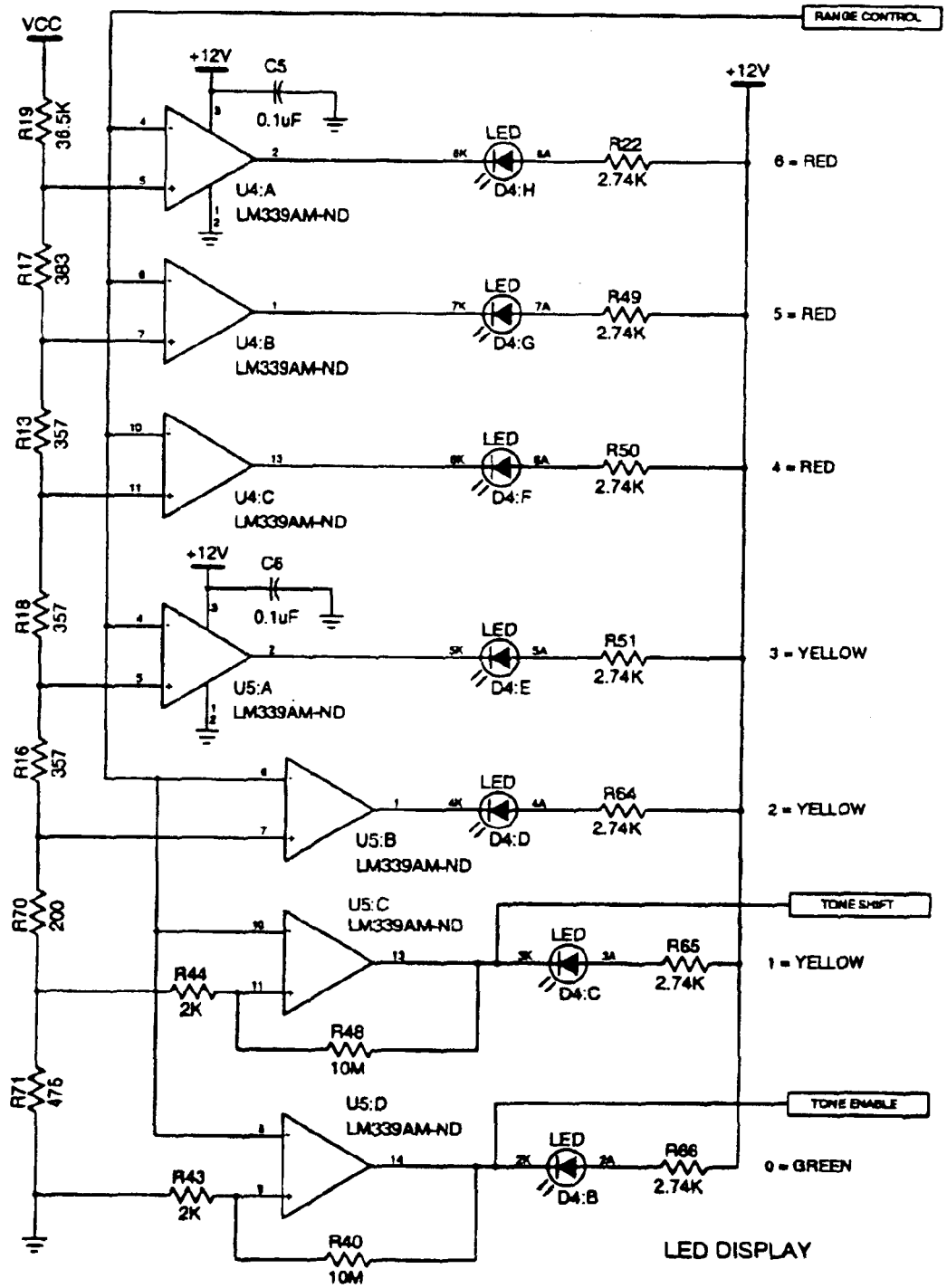
Figure 7B:
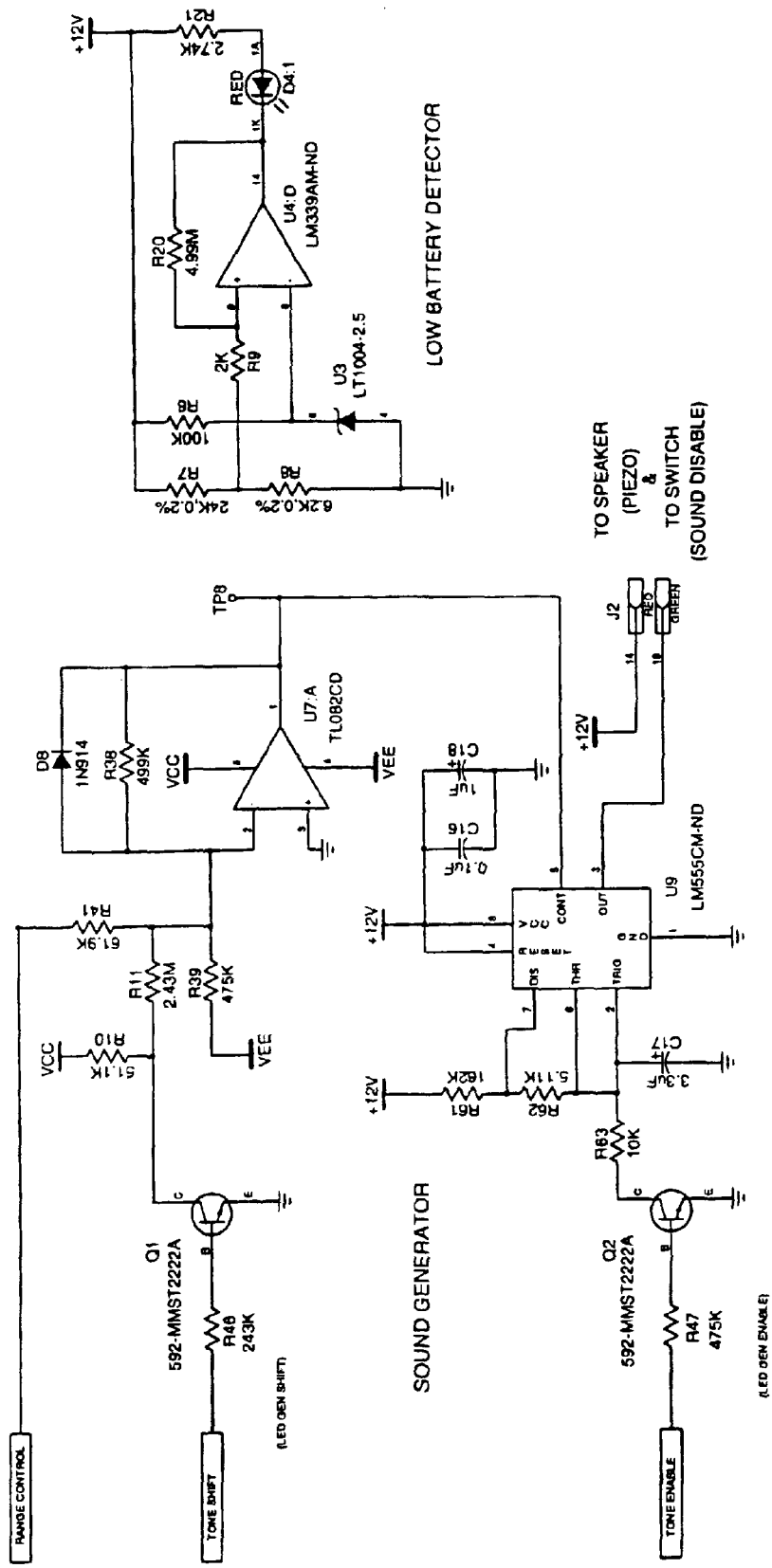

FIGS. 6 and 7 are schematics of the electronic circuitry within the novel detector and correlate to the block diagram of FIG. 5. Starting at the lower left of FIG. 6, battery power enters at J2 and directly powers the IR emitter and the 12 volt noncritical circuitry (e.g., digital circuits on FIG. 7). The battery drives the air-pump through regulator U10 which sets the air-flow rate. The battery also powers the IR sensor and analog circuitry in FIG. 6 through a dc/dc converter and LC filters on both +12 and −12 volt rails. A valid leak signal starts at the IR sensor at J1 (upper left of FIG. 6). A band-pass amplifier is formed by Integrated Circuit (IC) U6-A and associated components. This amplifier rejects the dc level and drift in the sensor, as well as higher frequency noise. The signal is further amplified and detected by IC U1-A and U1-B, and associated diodes and components. The circuit at IC U6-B provides the important signal "accumulator" function. R26 insures that D6 is always switched slightly "on" and ready to pass a small signal to C14 where it is temporarily held for further processing. This allows rapid detection of even a small leak, while accumulating more "signal" as the internally compensated IR sensor rebounds from a stronger signal. The detected (accumulator) signal is monitored by IC U8-A which subtracts off the dc level produced by the previous stage, provides a factory-adjustable gain at R31, and a user-adjustable "zero" at "POT" R46. IC U8-B is a follower to isolate the zero and gain adjust stage from the range switch stage at IC U7-B. The Range switch provides the user with 3 sensitivity levels labeled at "Large," "Medium," and "Small" leaks. The final analog output is clamped by low forward voltage diode D7 to keep the output form going much below zero volts in spite of wrong control settings or misuse.

The final analog output is passed to the digital circuit at the upper right corner of FIG. 7. At the left side of FIG. 7, this analog signal is compared with a non-linear resistive voltage divider via ICs U4 and U5 to provide the desired digital representation of the leak size on the LED display. D13 is a green LED that signals proper zero setting on a warmed up instrument at a steady-state condition (prior to detecting a leak). D12 to D4 form a bar-graph display of relative leak sizes. The sound generator consists of a chirp (pulse) generator at U9, a tone generator (e.g., 3000 Hz, which can be built into the Piezo speaker), an enable function, and a chirp rate shift function. The enable function is formed by Q2, which suppresses chirp output until the green LED D13 is on. The shift function is formed by Q2 to double the chirp rate (jump from approximately 1 Hz to approximately 2 Hz), as soon as the smallest leak is detected. The chirp rate is increased further with increasing analog (leak size) signal at U9 via U7-A.

Referring to FIGS. 6–7, low battery detection is provided by U4-D that compares the battery voltage with a precision voltage reference, through a divider set to trigger at the voltage at which a 12 volt NMH battery pack is about 90% discharged. This gives the user about 20–30 minutes warning that a recharge is needed very soon. Of course the warning could be set for earlier or later. The battery charging function is not represented on FIGS. 6–7. Charging can be provided through a current-sensing resistor that allows the charge LED to dim as the battery nears full charge, even using a low-cost non-regulated charger. The Industrial versions of the leak-detector can be very similar to FIGS. 6–7, except that the battery and charging functions are replaced by a 12.6 volt power supply, plus a larger air-pump regulator driving a long-life pump motor, and various "heavy duty" controls can be used.

Figure 8:
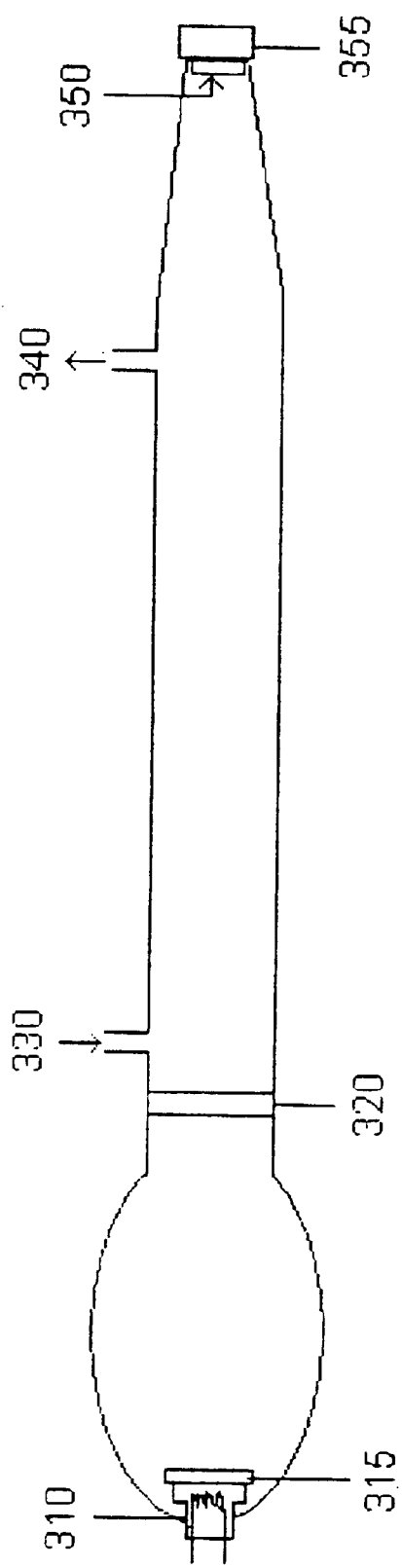
FIG. 8 shows another optical chamber that can be used with the novel detector.

FIG. 8 shows another optical chamber 300 that can be used with the novel detector. The signal to noise(S/N) ratio can be improved in the leak detector with a tandem optical bandpass filter configuration. Bandpass filter 1, 315 can pass in-band IR energy(approximately 8 to approximately 10 microns), but absorb higher-energy photons(less than approximately 8 microns), heats up, and re-emits this energy at a cooler temperature than the emitter. A substantial fraction of this secondary emission can be in the approximately 8 to approximately 10 micron band, and these photons can also pass through bandpass filter 2, 320(an approximately 8 to approximately 10 micron filter) as well. So for a given battery consumption, more approximately 8 to approximately 10 micron energy is in the gas chamber, to produce more signal, and less out-of-band energy gets through filter 2, 320 to contribute to noise a the IR sensor 350. IR sensor 310 can be a pair of parallel piezo capacitor elements that are coated optical black, Lithium Tanalate, and the like. Sample port 330, pump 340, IR chamber 305 and the other components conform to the similar described components previously described above. An additional filter 355 previously described can also be used.

During recent testing, the novel leak detector was able to operate in various temperature conditions ranging from approximately 32 to approximately 104 degrees F. The battery life of the detector lasted between approximately 4 to approximately 5 hours before needing to be recharged, and the sensor life was measured to have a life span of up to approximately 84 months(approximately 7 years). Response time for measuring leak contaminants such as refrigerant was within approximately 0.85 seconds of the time the leak detector was placed adjacent to the leak. Settings on the device allowed for at least three different setting positions. S covers small leaks of approximately 0.1 to approximately 1 oz per year. M covered medium leaks of approximately 0.4 to approximately 4 oz/yr. And L covered large leaks of approximately 1.6 to approximately 16 oz/yr.

Figure 9:
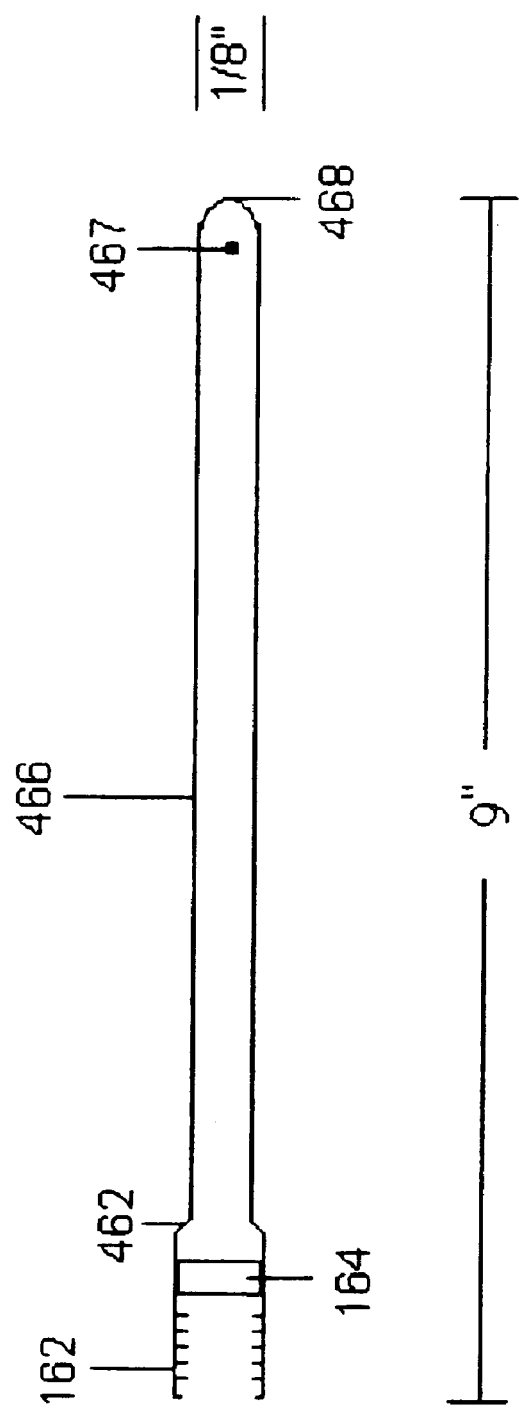
FIG. 9 shows a needle probe extension that can be used with the novel detector.

FIG. 9 shows an extra needle probe extension 460 that can be used with the novel detector 100 shown in FIG. 3. The needle probe extension 460 can be substantially tubular in configuration with a length of approximately 22.86 centimeters(approximately 9 inches), an outer diameter of approximately 0.3175 centimeters(approximately ⅛ of an inch) and an inside bore diameter of approximately 0.15875 centimeters (approximately 1/16 of an inch). Intake holes 467 can be set back from the end of the probe 468 to help prevent clogging. Opposite end 462 can include a threaded exterior or threaded interior surface to threadably attach to end 162 of the probe extension with an interior filter 164 shown in FIG. 3. Probe extension 460 can be formed from a pliable and strong material such as soft brass tubing which allows the probe extension to bend up to approximately 60 degrees without breaking apart, and allows it to be inserted into tight and narrow spaces for leak detection applications. Additional probe extensions up to an additional 30.48 centimeters (12 inches) can also be attached to the leak detector.

The novel detector can be used to detect various types of compounds such as gases and the like. Table 1 is a partial list of such compound materials that can be detected.

TABLE 1

| Gasses |
| --- |
| 1. HCFC- Hydrogenated Chorofluro carbon compounds, such as R-22 |
| 2. HFC- Fluorocarbon compounds, such as R-134a |
| 3. CFC- Chorofluoro carbon compounds, such as R 12 |
| 4. Refrigerant blends |
| 5. Propane |
| 6. Methane |
| 7. Gasoline |
| 8. Ammonia |
| 9. Acetone |
| 10. Benzene |
| 11. Bromine |
| 12. Carbon dioxide |
| 13. Carbon Monoxide |
| 14. Chlorine |
| 15. Fluorine |
| 16. Hydrogen Sulfide |
| 17. Isobutyl Alcohol |
| 18. Isopropyl Ether |

TABLE 1-continued

| Gasses |
| --- |
| 19. Pentane |
| 20. Sulfur Dioxide |
| 21. Sulfur Hexafluoride |
| 22. Trichloroethane |
| 23. Vinyl Acetate |
| 24. Vinyl Bromide |
| 25. Xylenes |

Although the leak detector device is shown using a chargeable battery, the detector can easily be operable to work off a power cord, and the like. For example, the detector device can be powered continuously from an AC/DC supply module that plugs into 115 Vac or 230 Vac.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A portable handheld infrared (IR) refrigerant gas leak detector, comprising in combination:

an infrared (IR) chamber;

means to solely draw a gas sample from a gas leak emanating from a single pressurized refrigerant gas source into the chamber;

means for detecting a selected compound from the sample in the chamber; and a handheld housing for supporting the chamber, the drawing means and the detecting means so that the detector is portable and is carryable in a single hand, wherein the detector detects whether there is a leak in the single pressurized gas source without introducing or mixing a secondary tracer gas within the device.

2. The portable detector of claim 1, wherein the IR chamber includes:

an IR emitter for emitting an IR beam;

an IR filter in the path of the beam; and an IR sensor for receiving the emitted beam; and and a reaction tube where the sample interacts with the IR beam.

3. The portable detector of claim 2, wherein the filter includes:

a broadband filter for passing wavelengths between approximately 8 to approximately 10 microns therethrough, and the sample is refrigerant.

4. The portable detector of claim 2, wherein the IR filter includes:

a narrowband filter which limits detection to (HFC) Hydrogenated Fluorocarbon compound refrigerants.

5. The portable detector of claim 2, wherein the IR filter includes:

a first broad band filter for filtering the beam before the beam passes into the chamber for removing portions of gas constituents from being selected for leak detection; and a narrow broad band filter for filtering the beam after the beam passes through the chamber and into the IR sensor.

6. The portable detector of claim 5, wherein the first broadband filter and the second broadband filter each pass in-band IR energy within the range of approximately 8 to approximately 10 microns.

7. The portable detector of claim 2, further comprising:

an audio output to the detector for emitting an audio signal from a detected leak, the audio output having a zero control setting having a substantially constant approximately 1 Hz chirp signal, the audio output digitally shifting to a 2 Hz chirp rate upon detection of the gas leak, and the audio output increasing the chirp rate above approximately 2 Hz in proportion to size of the gas leak being detected.

8. The portable detector of claim 2, further comprising:

a signal detection accumulator with a forward biased detector circuit; and a zero circuit referenced to approximately a circuit ground instead of referenced between supply rails.

9. The portable detector of claim 2, further comprising:

a window adjacent to the emitter which reduces convection noise and increases in-band IR radiation signal strength.

10. The portable detector of claim 1, wherein the drawing means includes:

an air pump having a continuous sampling rate of approximately hundreds of cc/min so that the detector does not have to be within approximately 0.635 centimeters (approximately 0.25 inch) of a refrigerant leak source, and the sample includes an air sample that includes the refrigerant leak source.

11. The portable detector of claim 1, wherein the IR leak detector includes:

a pyroelectric sensor.

12. The portable detector of claim 11, wherein the sensor is selected from at least one of: a pair of back to back piezo capacitor elements.

13. The portable detector of claim 1, further comprising:

an elongated continuously cylindrical and detachable needle probe extension for attaching adjacent to the drawing means for allowing the detector to take the sample in tight spaces, the needle probe extension having an inlet opening adjacent to and not at a tip end of the needle probe extension.

14. The portable detector of claim 1, wherein the IR chamber includes:

a gold plated plastic infrared (IR) optical chamber.

* * * * *

(12) INTER PARTES REEXAMINATION CERTIFICATE (0168th)
United States Patent
Williams, II et al.

(10) Number: US 6,791,088 C1
(45) Certificate Issued: Jun. 29, 2010

(54) INFRARED LEAK DETECTOR

(75) Inventors: William J. Williams, II, Melbourne, FL (US); Glenn A. Dejong, Merritt Island, FL (US)

(73) Assignee: Twin Rivers Engineering, Inc., Melbourne, FL (US)

Reexamination Request:
No. 95/000,233, Mar. 13, 2007

Reexamination Certificate for:
Patent No.: 6,791,088
Issued: Sep. 14, 2004
Appl. No.: 10/138,399
Filed: May 3, 2002

Related U.S. Application Data

(60) Provisional application No. 60/288,857, filed on May 4, 2001.

(51) Int. Cl.
*G01M 3/04* (2006.01)
*G01N 21/35* (2006.01)
*G01N 21/11* (2006.01)
*G01N 21/31* (2006.01)

(52) U.S. Cl. ................................ 250/343; 250/345
(58) Field of Classification Search .................. None
See application file for complete search history.

(56) References Cited

U.S. PATENT DOCUMENTS

| | | | |
|---|---|---|---|
| 3,742,475 A | | 6/1973 | Liebermann |
| 5,198,774 A | | 3/1993 | Williams, II |
| 5,264,833 A | * | 11/1993 | Jeffers et al. ............... 340/632 |
| 5,265,483 A | | 11/1993 | Farrell |
| 5,324,951 A | | 6/1994 | Kocache |
| 5,497,003 A | * | 3/1996 | Baliga et al. ............ 250/338.3 |
| 5,563,617 A | | 10/1996 | Redfern |
| 5,608,219 A | | 3/1997 | Aucremanne |
| 5,610,398 A | | 3/1997 | Anderson |
| 5,798,696 A | * | 8/1998 | Wong ........................ 340/605 |
| 5,834,777 A | | 11/1998 | Wong |
| 5,838,016 A | | 11/1998 | Johnson |
| 5,874,737 A | | 2/1999 | Bytyn |

(Continued)

OTHER PUBLICATIONS

Sensor Specfications for Draeger Pac III, MiniWarn and X-am Gas Detectors (revised Jan. 23, 2007 (pp. 1–7), downloaded form internet at http://www.afcintl.com/draegersensor.htm Jun. 4, 2007.*
Brian R. Kinkade, Bringing Nondispersive IR Spectroscopic Gas Sensors to the Mass Market, Sensors Magazines Online, Aug. 2000, (10 pages).
Inficon, HLD4000 Product Manual, Aug. 1993, (14 pages).

*Primary Examiner*—Albert J Gagliardi

(57) ABSTRACT

A leak detector using an infrared emitter and pyroelectric sensor to form an instrument for identifying the presence and concentration of a selected material type gas compound, such as a refrigerant gas compound within a given sample, such as a sample of ambient air. For the detection, a radiation flux coming from an infrared emitter penetrates the sample, which is analyzed spectrally, and results in a wave lengthspecific signal being generated at the output of the detector. By controlling the type of optical filter, the radiation energy is controlled at a selected wavelength, to ensure coverage of all selected compounds. For refrigerants, the selected wavelength can be between approximately 8 to approximately 10 microns in the wavelength range. This selected wavelength obscures other signals, thus minimizing false alarms. By not chopping or pulsing the emitter, the leak detector has a faster response time with no adverse impacts on the accuracy of the compound material being detected. To further minimize false alarms and to ensure that the emitter does not come in contact with the sample gas, an additional filter can be positioned in the optical path. For refrigerant compounds, the filter can block out signals below approximately 6 microns. For detecting refrigerants, two filters can be used: 1) a broadband filter to allow detection of all refrigerants currently on the market, and 2) a narrowband filter to limit detection only to $R134_a$ which possesses a narrow wavelength, so that detection of other compounds (or contaminants) can be minimized.

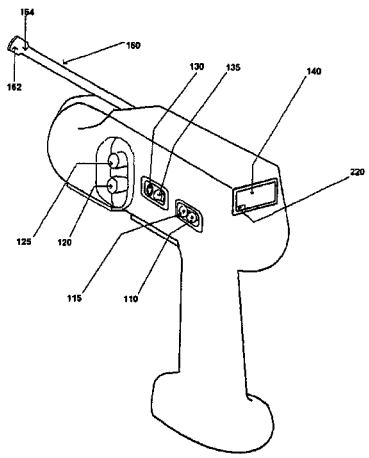

U.S. PATENT DOCUMENTS

| | | | |
|---|---|---|---|
| 5,889,199 A | | 3/1999 | Wong |
| 6,100,529 A | | 8/2000 | O'Dwyer |
| 6,112,532 A | * | 9/2000 | Bakken .................. 62/174 |
| 6,255,652 B1 | | 7/2001 | Moyer |
| 6,362,741 B1 | * | 3/2002 | Hickox et al. ............ 340/605 |
| 6,392,234 B2 | * | 5/2002 | Diekmann ............ 250/338.3 |
| 6,410,918 B1 | | 6/2002 | Kouznetsov |
| 6,469,303 B1 | | 10/2002 | Sun |

* cited by examiner

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-14 are cancelled.

\* \* \* \* \*